United States Patent
Bratteli et al.

(10) Patent No.: US 6,394,958 B1
(45) Date of Patent: May 28, 2002

(54) APPARATUS AND METHOD FOR BLOOD PRESSURE PULSE WAVEFORM CONTOUR ANALYSIS

(75) Inventors: Christopher W. Bratteli, Fridley; Jay N. Cohn, Minneapolis; Stanley M. Finkelstein, St. Louis Park; Dennis J. Morgan, Crystal, all of MN (US)

(73) Assignee: Hypertension Diagnostics, Inc., Eagan, MN (US)

( * ) Notice: Subject to any disclaimer, the term of this patent is extended or adjusted under 35 U.S.C. 154(b) by 0 days.

(21) Appl. No.: 09/434,077

(22) Filed: Nov. 5, 1999

Related U.S. Application Data

(63) Continuation of application No. 09/045,420, filed on Mar. 20, 1998.

(51) Int. Cl.$^7$ ................................. A61B 5/02
(52) U.S. Cl. ................. 600/485; 600/481; 600/523; 128/898
(58) Field of Search ................. 600/300, 301, 600/481–486, 500–508, 513–515

(56) References Cited

U.S. PATENT DOCUMENTS

| | | | |
|---|---|---|---|
| 3,651,353 A | 3/1972 | Hugli et al. | |
| 4,409,983 A | 10/1983 | Albert | |
| 4,431,873 A | 2/1984 | Dunn et al. | |

(List continued on next page.)

FOREIGN PATENT DOCUMENTS

| | | | |
|---|---|---|---|
| EP | 0357275 A1 | 3/1990 | ............ A61B/5/11 |
| WO | 87/02233 | 4/1987 | ............ A61B/7/04 |
| WO | 92/09232 | 6/1992 | ......... A61B/5/0255 |
| WO | 94/05207 | 3/1994 | ............ A61B/7/04 |
| WO | 95/06525 | 3/1995 | ............. B06B/1/06 |

OTHER PUBLICATIONS

"Acoustic Contact Sensor", *Apollo Research Corp.,* Model 701010, 1–5, (1997).
"Aging Arteries", *Harvard Heart Letter,* 8(2), 4 pgs., (Oct. 1997).
"Guide to Modern Piezoelectric Ceramics", Advertising Material from Morgan Matroc, Inc. (undated), 6 pages.
"Harvard Heart Letter", *Harvard Medical School,* 7(7), 5 pgs., (Mar. 1997).
"Nellcor's N–CAT Continuous Noninvasive Blood Pressure Monitor, Model N–500", Product Publication by Nellcor, Inc., 9 pages, (1991).
"Non–Invasive Arterial Waveform Analysis and Blood Pressure Measurement", Pulse Dynamic Oscillometrics Clinical Information, Pulse Metric, Inc., San Diego, CA, 4.
"Non–Invasive Blood Pressure/Pulse Rate Monitoring and Recording System", , Portfolio™ Health Series, 6 pages.
Bing, et al., "Reversal of Acetylcholine Effect on Atherosclerotic Coronary Arteries by Estrogen: Pharmacologic Phenomenon of Clinical Importance?", *Journal of the American college of Cardiology,* 3 pages, (Aug. 1992).

(List continued on next page.)

*Primary Examiner*—John P. Lacyk
*Assistant Examiner*—Michael Astorino
(74) *Attorney, Agent, or Firm*—Schwegman, Lundberg, Woessner & Kluth, P.A.

(57) ABSTRACT

Methods and apparatus for processing an arterial blood pressure waveform to extract clinically useful information on the state of the cardiovascular system are disclosed herein. In order to obtain the parameters of the modified Windkessel model, the diastolic portion of a subject's blood pressure waveform is scanned over a plurality of ranges and the range that produces the best fit of data and lowest error estimates are selected. In addition, multiple empirically determined starting values of the 'A' parameters are used to find the best fit of the model data to the actual arterial blood pressure waveform data.

30 Claims, 9 Drawing Sheets

- A – UPSTROKE MARK (ONSET OF SYSTOLIC) THIS IS THE POINT ASSIGNED TO THE ITH INDEX AT WHICH THE PRESSURE CHANGE BETWEEN THE ITH AND ITH +5TH DATA POINTS EXCEEDS 10 mmHg B – SYSTOLE MARK (PEAK SYSTOLE).
- B – THIS IS THE PEAK VALUE OF THE BEAT
- C – DICROTIC NOTCH MARK (ONSET OF DIASTOLE) THIS IS THE LOCAL MINIMUM FOLLOWING PEAK SYSTOLE IF IT OCCURS OR THE INFLECTION POINT.
- D – DIASTOLE MARK (END DIASTOLE) THIS IS THE POINT AT WHICH THE DIASTOLIC DECAY STOP ITS MONOTONIC DECAY.
- L–R – THE NEAR NOTCH SCAN RANGE IS A REGION AROUND C BOUNDED BY THE ZERO CROSSING OF THE SECOND DERIVATIVE OF THIS WAVE FORM PRIOR TO C AND THE ZERO CROSSING OF THE SECOND DERIVATIVE OF THIS WAVE FORM FOLLOWING C.

U.S. PATENT DOCUMENTS

| | | | |
|---|---|---|---|
| 4,672,976 A | | 6/1987 | Kroll |
| 4,784,154 A | | 11/1988 | Shirley et al. |
| 4,889,133 A | * | 12/1989 | Nelson et al. .............. 600/494 |
| 4,947,859 A | | 8/1990 | Brewer et al. |
| 4,949,710 A | * | 8/1990 | Dorsett et al. .............. 600/494 |
| 5,035,247 A | | 7/1991 | Heimann |
| 5,054,493 A | * | 10/1991 | Cohn et al. ................. 600/481 |
| 5,211,177 A | | 5/1993 | Chesney et al. |
| 5,241,964 A | * | 9/1993 | McQuilkin .................. 600/500 |
| 5,316,004 A | | 5/1994 | Chesney et al. |
| 5,337,750 A | * | 8/1994 | Walloch ..................... 600/494 |
| 5,524,637 A | | 6/1996 | Erickson |
| 5,544,651 A | | 8/1996 | Wilk |
| 5,551,437 A | | 9/1996 | Lotscher |
| 5,551,438 A | | 9/1996 | Moses |
| 5,560,366 A | | 10/1996 | Barada et al. |
| 5,577,508 A | | 11/1996 | Medero |
| 5,584,298 A | | 12/1996 | Kabal |
| 5,590,661 A | | 1/1997 | Ohmori et al. |
| 5,592,401 A | | 1/1997 | Kramer |
| 5,617,868 A | | 4/1997 | Harada et al. |
| 5,623,933 A | | 4/1997 | Amano et al. |
| 5,638,823 A | | 6/1997 | Akay et al. |
| 5,640,964 A | | 6/1997 | Archibald et al. |
| 5,642,733 A | | 7/1997 | Archibald et al. |
| 5,647,369 A | | 7/1997 | Petrucelli et al. |
| 5,649,542 A | | 7/1997 | Archibald et al. |
| 5,671,750 A | | 9/1997 | Shinoda |
| 5,704,362 A | | 1/1998 | Hersh et al. |
| 5,752,919 A | * | 5/1998 | Schrimpf .................... 600/493 |
| 5,908,027 A | | 6/1999 | Butterfield et al. ......... 128/672 |

OTHER PUBLICATIONS

Brinton, et al., "Arterial Compliance by Cuff Sphygmomanometer", *Hypertension,* 28(4), Application to Hypertension and Early Changes in Subjects at Genetic Risk, 599–603, (Oct. 1996).

Brinton, et al., "The Development and Validation of a New Non–invasive Method to Evaluate Ventricle Function During Routine Blood Pressure Monitoring", *American Journal of Hypertension,* 10(4) Part 2 (Abstract Issue), 2 pages, (1997).

Cohn, J.N., et al., "Noninvasive Pulse wave Analysis for the early detection of Vascular Disease", *Hypertension,* 26, 503–508, (Sep., 1995).

Glasser, et al., "Vascular Compliance and Cardiovascular Disease", *AJH,* 10(10), Part 1, 1175–1189, (Oct. 1997).

Kluger, J., "Beyond Cholesterol", *Time,* 48, (Aug. 4, 1997).

McVeigh, et al., "Vascular Abnormalities Associated with Long–term Cigarette Smoking Identified by Arterial Waveform Analysis", *The American Journal of Medicine,* 102, 227–231, (Mar. 1997).

Rajkumar, et al., "Hormonal Therapy Increases Arterial Compliance in Postmenopausal Women", *JACC,* 30(2), 350–356, (Aug. 1997).

Simon, et al., "Detection of Preclinical Atherosclerosis May Optimize the Management of Hypertension", *AJH,* 10(7) Part 1, 813–824, (Jul. 1997).

Yoshizawa, et al., "Classical but Effective Techniques for Estimating Cardiovascular Dynamics", *IEEE Engineering in Medicine & Biology Magazine,* 16(5), 106–112, (Sep.–Oct. 1997).

* cited by examiner $C_1$ = PROXIMAL ARTERIAL COMPLIANCE (ml/mm Hg)
$C_2$ = DISTAL ARTERIAL COMPLIANCE (ml/mm Hg)
L = INERTANCE (mm Hg · $S^2$/ml)
$P_1$ = PROXIMAL ARTERIAL (AORTIC) PRESSURE (mm Hg)
$P_2$ = DISTAL ARTERIAL (BRACHIAL) PRESSURE (mm Hg)
R = PERIPHERAL RESISTANCE (DYNES·s·$cm^{-5}$)

GENERAL DESCRIPTION OF ANALYSIS PROCESS

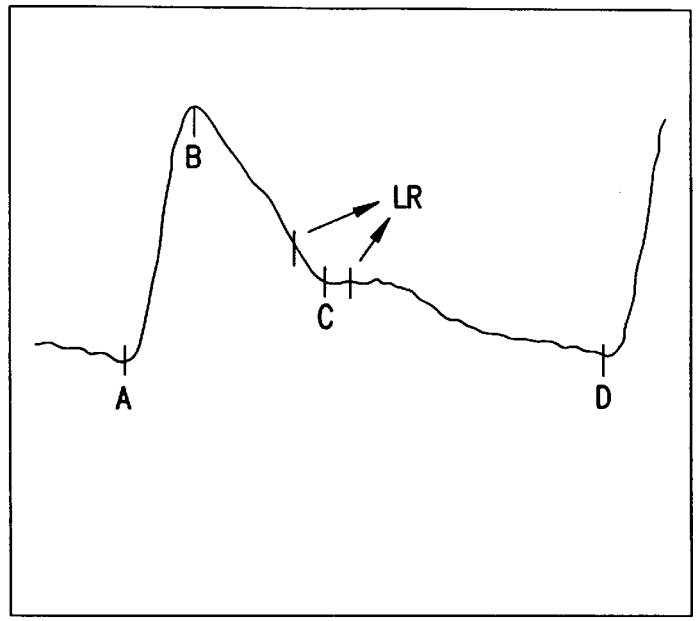

- A – UPSTROKE MARK (ONSET OF SYSTOLIC) THIS IS THE POINT ASSIGNED TO THE ITH INDEX AT WHICH THE PRESSURE CHANGE BETWEEN THE ITH AND ITH +5TH DATA POINTS EXCEEDS 10 mmHg B – SYSTOLE MARK (PEAK SYSTOLE).
- B – THIS IS THE PEAK VALUE OF THE BEAT
- C – DICROTIC NOTCH MARK (ONSET OF DIASTOLE) THIS IS THE LOCAL MINIMUM FOLLOWING PEAK SYSTOLE IF IT OCCURS OR THE INFLECTION POINT.
- D – DIASTOLE MARK (END DIASTOLE) THIS IS THE POINT AT WHICH THE DIASTOLIC DECAY STOP ITS MONOTONIC DECAY.
- L-R – THE NEAR NOTCH SCAN RANGE IS A REGION AROUND C BOUNDED BY THE ZERO CROSSING OF THE SECOND DERIVATIVE OF THIS WAVE FORM PRIOR TO C AND THE ZERO CROSSING OF THE SECOND DERIVATIVE OF THIS WAVE FORM FOLLOWING C.

FIG. 4

APPARATUS AND METHOD FOR BLOOD PRESSURE PULSE WAVEFORM CONTOUR ANALYSIS

This application is a continuation of U.S. Ser. No. 09/045,420, filed Mar. 20, 1998.

FIELD OF THE INVENTION

This invention relates to the field of medical diagnosis, and more specifically, to a method and apparatus for blood pressure pulse waveform contour analysis.

BACKGROUND OF THE INVENTION

U.S. Pat. No. 5,211,177 (incorporated herein by reference) discloses method and apparatus for measuring properties of the human vasculature using an electrical analog model of vascular impedance. These properties include the compliance of large and small vessels, and systemic resistance. These measurements and others obtained from the model can in turn be used to diagnose states of health or disease, and to assess the effectiveness of treatment regimes. For example, see Finkelstein S. M., Collins V. R., Cohn J. N., *Arterial vascular compliance response to vasodilators by Fourier and pulse contour analysis*, Hypertension 1988:12:380–387, the entire disclosure of which is incorporated herein by reference.

The simplest model for representing the time-varying pressure behavior of the arterial blood pressure waveform during the diastolic decay phase of the cardiac cycle is a first-order model. The analog model that represents this behavior contains a single "active" element (capacitance) and a passive element (resistance). The model only accounts for the pure exponential decay present in the waveform. An improvement to this model that better accounts for the observed shape of the diastolic decay in humans is a third-order model, for example, the modified Windkessel model. The analog model that represents this behavior contains three active elements, two capacitors (compliance) separated by an inductor (inertance of the blood) and a passive resistance (systemic vascular resistance) element. This is the model preferred in the system of U.S. '177, and employed in the approach of the example embodiment of the present invention described herein.

U.S. '177 describes a time-domain pulse contour analysis employed to extract useful information from the arterial blood pressure waveform. This pulse contour analysis employs a curve fitting approach applied to the diastolic blood pressure decay and subsequent use of the modified Windkessel electrical analog model of the vasculature to give physiological meaning to the analysis in terms of measures of systemic arterial performance.

The modified Windkessel model of the arterial system is shown in FIG. 1. The model includes components $P_1$, $P_2$, $C_1$, $C_2$, L and R in which:

$C_1$=proximal or capacitive compliance (ml/mm Hg)
$C_2$=distal or reflective or oscillatory compliance (ml/mm Hg)
L =inertance (mm Hg/(ml/s$^2$))
$P_1$=proximal or aortic arterial pressure (mm Hg)
$P_2$ distal or peripheral artery pressure (mm Hg)
R=peripheral resistance (dynes s cm$^{-5}$)

As taught, for example, by Goldwyn and Watt in I.E.E.E. Trans. Biomed. Eng. 1967; 14:11–17, the disclosure of which is hereby incorporated by reference herein, $P_2$ of the modified Windkessel model may be represented by the third order equation:

$$P(t)=A_1 e^{-A_2 t}+A_3 e^{-A_4 t}\cos(A_5 t+A_6)$$

wherein:

$$C_1 = \frac{mn-p}{mp}\frac{1}{R}$$

$$C_2 = \frac{1}{m}\frac{1}{R}$$

$$L = \frac{m^2 R}{mn-p} \text{ and}$$

$$m = A_2 + 2A_4$$

$$n = 2A_2 A_4 + A_4^2 + A_5^2 \text{ and}$$

$$p = A_2(A_4^2 + A_5^2)$$

Thus, knowing R, which can be calculated from cardiac output and mean arterial pressure as follows:

$$R = \frac{\text{mean arterial pressure mmHg}}{\text{cardiac output (milliliters/second)}}$$

$C_1$, $C_2$ and L are readily calculated.

Pulse contour analysis as described in U.S. '177 begins with the acquisition of digital representation of the arterial waveform. A number of consecutive beats are acquired, preferably for about 30 seconds, and stored for processing. These beats are then screened to eliminate abnormally fast or slow beats, or beats of abnormally high or low pressure. This screening preferably yields at least six to ten consecutive beats to be used for further analysis. Using a software algorithm, this representation is then marked to identify the diastolic portion of the arterial blood pressure waveform.

In U.S. '177, a curve fitting algorithm, such as the Gauss-Newton parameter estimating algorithm, is then applied to the marked diastolic data set of the waveform to ascertain the 'A' coefficients of the modified Windkessel model. An automatic stopping procedure was employed to stop iteration when an acceptable level of error was reached or when convergence slowed below a preset threshold. Also, U.S. '177 proposed that when the process started to diverge it returned to the previous best case. Additionally, the routine included a weighted iteration interval to improve convergence. Using a measure of cardiac output and mean arterial pressure to calculate R, the modified Windkessel parameters $C_1$, $C_2$ and L could then be calculated as well. In U.S. '177, it is contemplated that the parameters R, $C_1$, $C_2$ and L are calculated for each beat in the set under analysis, and subsequently averaged to produce mean values more reliable for accuracy than any of the individual values. Alternatively, U.S. '177 teaches that median values can be selected.

While the approach taught in U.S. '177 produces useful results, it has been a goal of researchers to continue to perfect and improve waveform analysis, in order to more reliably obtain measurements of vascular impedance. To this end, a number of areas for improvement have been identified and presented herein.

SUMMARY OF THE INVENTION

The present invention provides a number of improvements to the approaches to waveform analysis set forth in U.S. '177. These improvements include analyzing individual beats and determining resultant values as a weighted average of the individual beat values based on their error estimates and quality of curve fit. Another improvement provides for better detection of the onset of diastole by scanning over a near-notch region. Yet another improvement provides for selecting independent models (i.e., final 'A' parameter sets generated from curve fitting) for each of the Windkessel model components based on minimizing the coefficient of variation (CV) of the components' measures. The use of a set of empirically determined initial 'A' parameters is another improvement. Yet another improvement includes a procedure for better locating the end of diastole. A still further improvement provides for selection of beats for analysis based on heart rate variability.

BRIEF DESCRIPTION OF THE DRAWINGS

FIG. 4 illustrates an arterial blood pressure waveform and points of interest therein;

DESCRIPTION OF PREFERRED EMBODIMENTS

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

Figure 1:
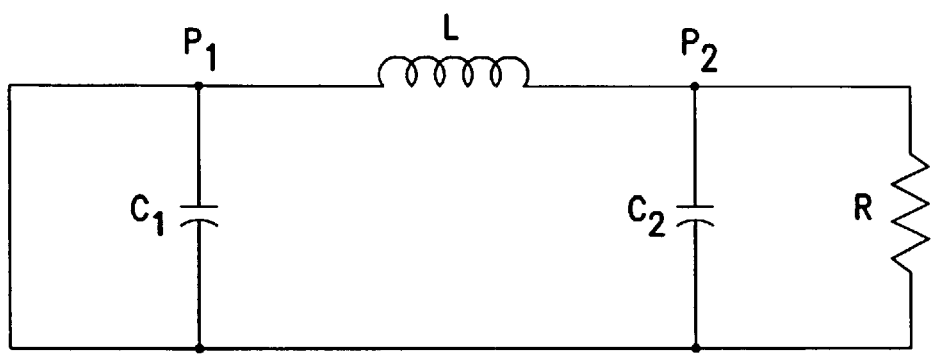
FIG. 1 illustrates the prior art modified Windkessel model.
Figure 2:
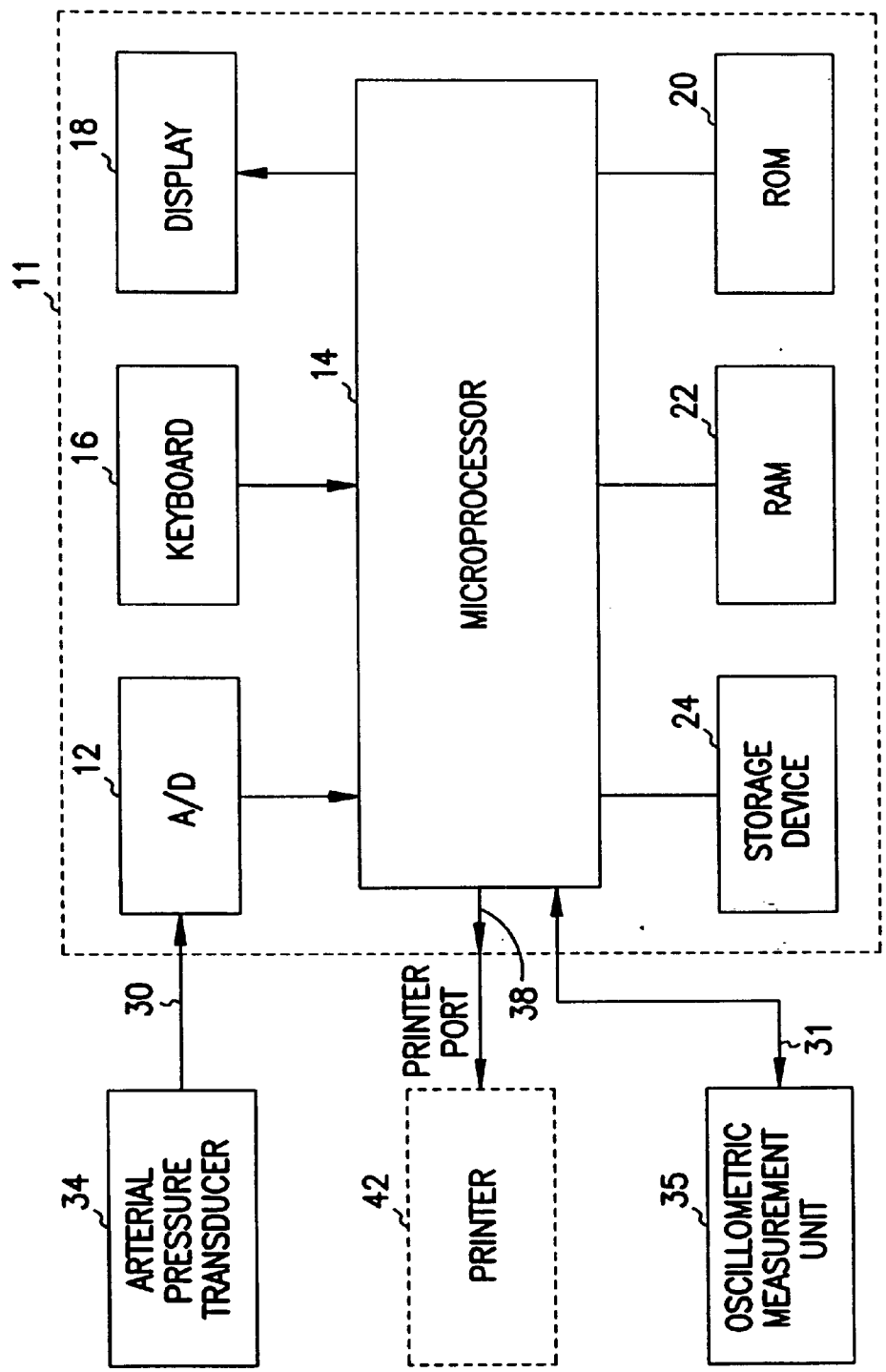
FIG. 2 illustrates an example of a vascular impedance determining device according to the present invention.

Referring to FIG. 2, there is illustrated a simplified example of the apparatus for measuring vascular compliance. The instrument 10 includes a transducer unit 34, an oscillometric cuff blood pressure measurement unit 35, a computer system 11, and a printer 42. System 11 includes an analog to digital converter (A/D) 12, preferably 16-bit, and a micro-processor unit 14, for example a S-MOS Cardio I/O 486 75 MHz (available from S-MOS Systems, Inc., of San Jose, Calif.), a keyboard or similar input device 16 such as a touch sensitive screen and corresponding user interface, a display 18 such as a Planar™ electroluminescent display (available from Planar Systems, Inc., of Beaverton, Oreg.), a ROM 20, a flash RAM 22 and a storage device 24. An input port 30 is provided to receive analog signal input from an arterial pressure transducer unit 34. In addition, there is provided an input port 31 for data received from an oscillometric cuff blood pressure measurement device 35. Microprocessor 14 includes an output port 38 connected to optional printer 42.

Transducer unit 34 and related accessories are preferably those shown in co-pending U.S. Pat. No. 6,159,166, issued Dec. 12, 2000 entitled "Sensor and Method for Sensing Arterial Pulse Pressure" and filed on even date herewith, and U.S. Pat. No. 6,132,383, issue Oct. 17, 2000 entitled "Apparatus and Method for Holding and Positioning an Arterial Pulse Pressure Sensor" and filed on even date herewith, the contents of both said applications being incorporated herein by reference. Oscillometric cuff pressure measurement unit 35 is preferably an OEM blood pressure module, such as those sold by Colin Medical Instruments, Inc., of San Antonio, Tex.

Other alternative means of measuring the arterial waveform are disclosed in U.S. '177. Moreover, the arterial waveform may also be obtained invasively, if desired, although this is not believed to be preferred from a cost, medical risk and patient and healthcare professional convenience perspective, using, for example, a Statham P23Db pressure transducer as unit 34. If obtained invasively, preferably, such a transducer would be connected to a patient's brachial or radial artery via an 18-gauge, 2-inch Teflon catheter. This catheter-transducer system should have an undamped natural frequency higher than 25 Hz and a damping coefficient less than 0.5, providing an acceptable frequency response. It shall be understood, however, that while the brachial or radial artery is preferred, other central or peripheral arterial locations for obtaining the blood pressure waveforms can be substituted.

Figure 3:
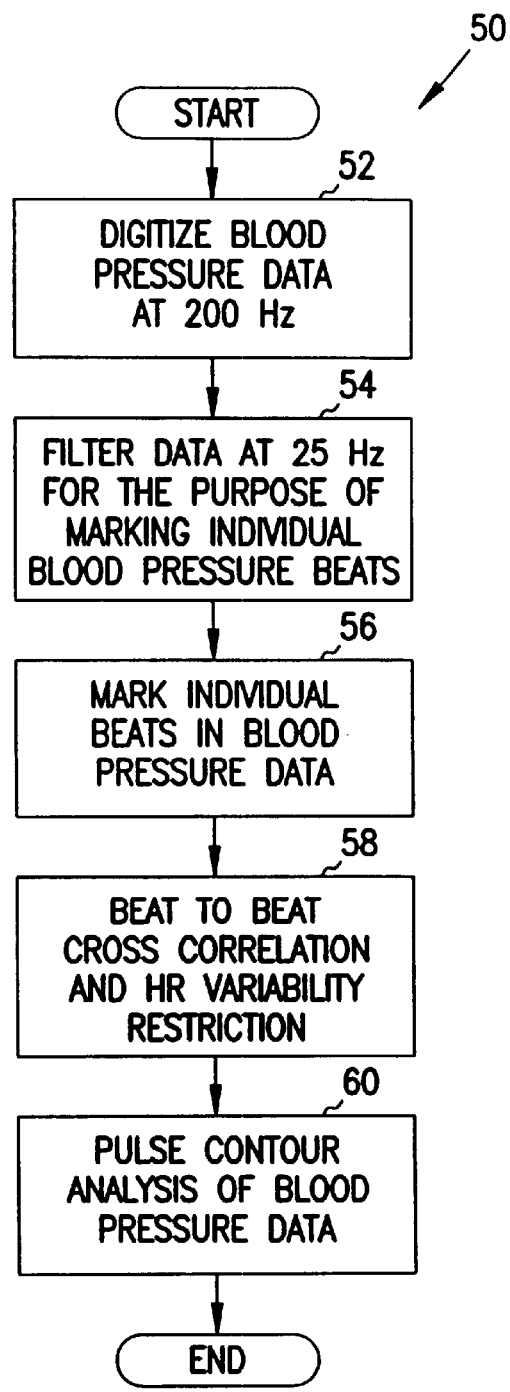
FIG. 3 is an overview of an example process for waveform analysis according to the present invention.

Referring to FIG. 3, there is shown an overview of the process 50 of arterial waveform analysis according to one example embodiment of the present invention. FIG. 3 is representative of the process of arterial waveform analysis and also the underlying computer program which directs the execution of the process, through microprocessor 14, in system 10. Process 50 is carried out under program control by microprocessor 14 and/or its computer peripherals. The program can be stored in whole or in part in ROM 20 or in storage device 24 or RAM 22.

The process 50 begins with digitizing an analog blood pressure waveform (52), preferably at 200 Hz, with a 16-bit resolution. According to one example embodiment, waveforms are collected for a thirty (30) second duration. This data can be stored in RAM 22 or in storage device 24. In addition to blood pressure waveform data, it is also necessary to obtain oscillometric cuff pressure data, input at port 31, just preceding the time of waveform acquisition in order to calibrate the waveform in terms of pressure in mm Hg.

Next, the data is filtered (54), preferably using an eight (8) pole, 25 Hz low. pass Butterworth filter with an attenuation of 6.0206 dB at the corner frequency, for the purpose of marking individual beats. The initial filtering at 25 Hz provides sufficient smoothing of the blood pressure data to enable consistent marking for the upstroke (A), peak (B), and end diastolic point (D) for each beat. These locations are identified without the use of derivatives of the pressure data. In order to identify the dicrotic notch (C) and the left and right scan points bracketing the notch (L-R), termed the near-notch region (NNR), derivatives of the pressure waveforms are utilized. Digital derivatives inherently amplify noise in the data and thus to minimize the noise in the derivatives of the blood pressure waveforms the portion of the waveform between systole and end diastole for each beat is further filtered using an eight (8) pole, 15 Hz low pass Butterworth filter with an attenuation of 6.0206 dB at the corner frequency.

After the marks have been identified, the digitized waveform data is converted to pressure in mmHg for analysis using a two point calibration. In one embodiment, the median systolic and median upstroke values are used together with the systolic and diastolic measurements of blood pressure obtained from the oscillometric cuff pressure measurement unit 35 to calibrate the pressure data. In another embodiment the median mean waveform value and the median upstroke waveform value together with the mean pressure and diastolic pressure determined from the oscillometric cuff pressure measurement unit 35 could be utilized to calibrate the data.

A beat to beat cross correlation is then performed using Pearson's cross-correlation to determine a dominant family of beats, and a heart rate variability restriction is applied (58) in order to select a group of blood pressure beats for further analysis, as described more fully below. Preferably, no less than five (5) and no more than ten (10) beats are selected. However, the exact number selected is not critical. The last step in the illustrated process is the analysis of the marked and selected beats (60) to determine the sought after parameters of cardiovascular profile using, for example, the modified Windkessel model.

Figure 5A:
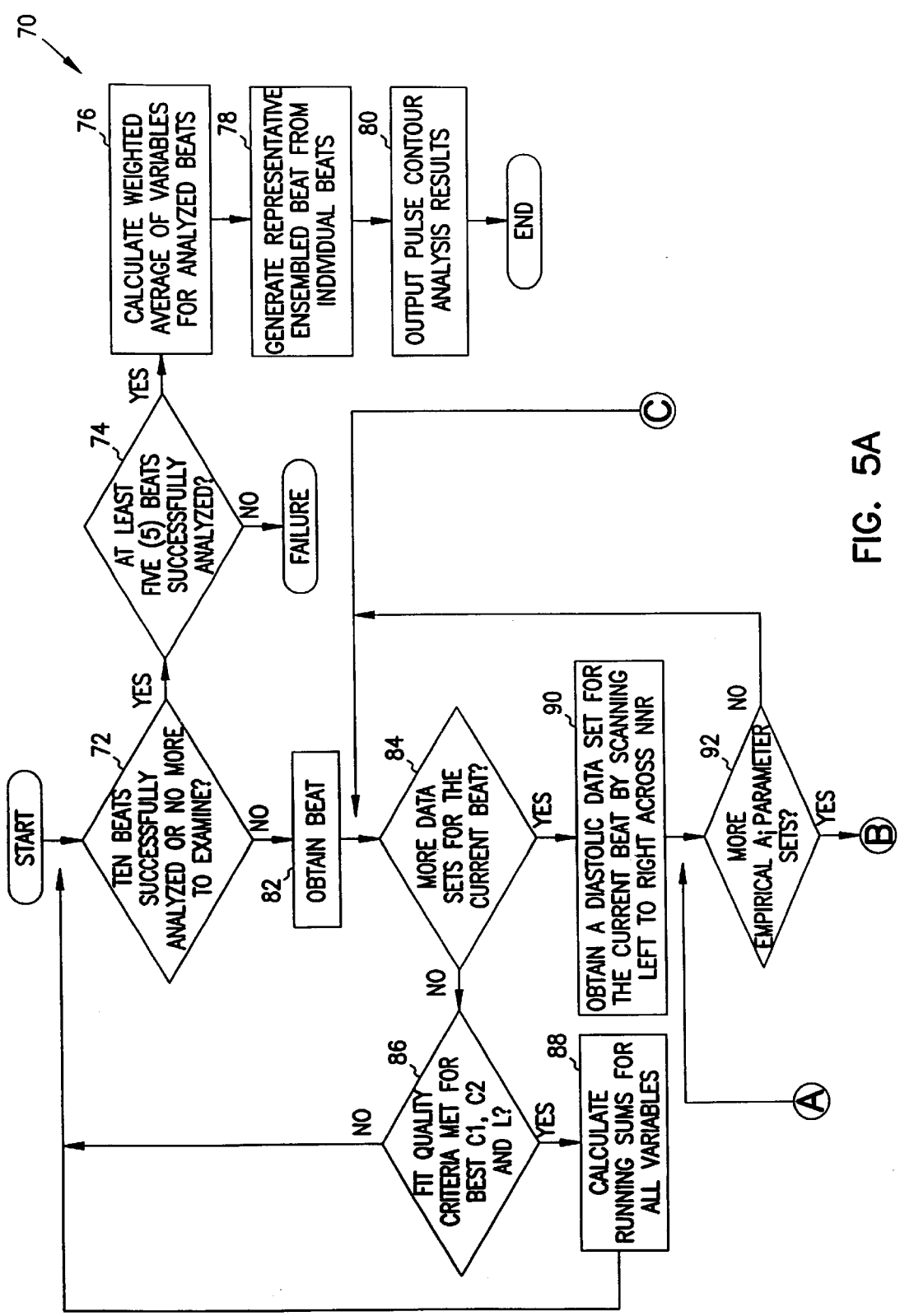
FIGS. 5A and 5B together form FIG. 5, which is a more detailed flowchart of an example process for pulse contour analysis according to the present invention.
Figure 5B:
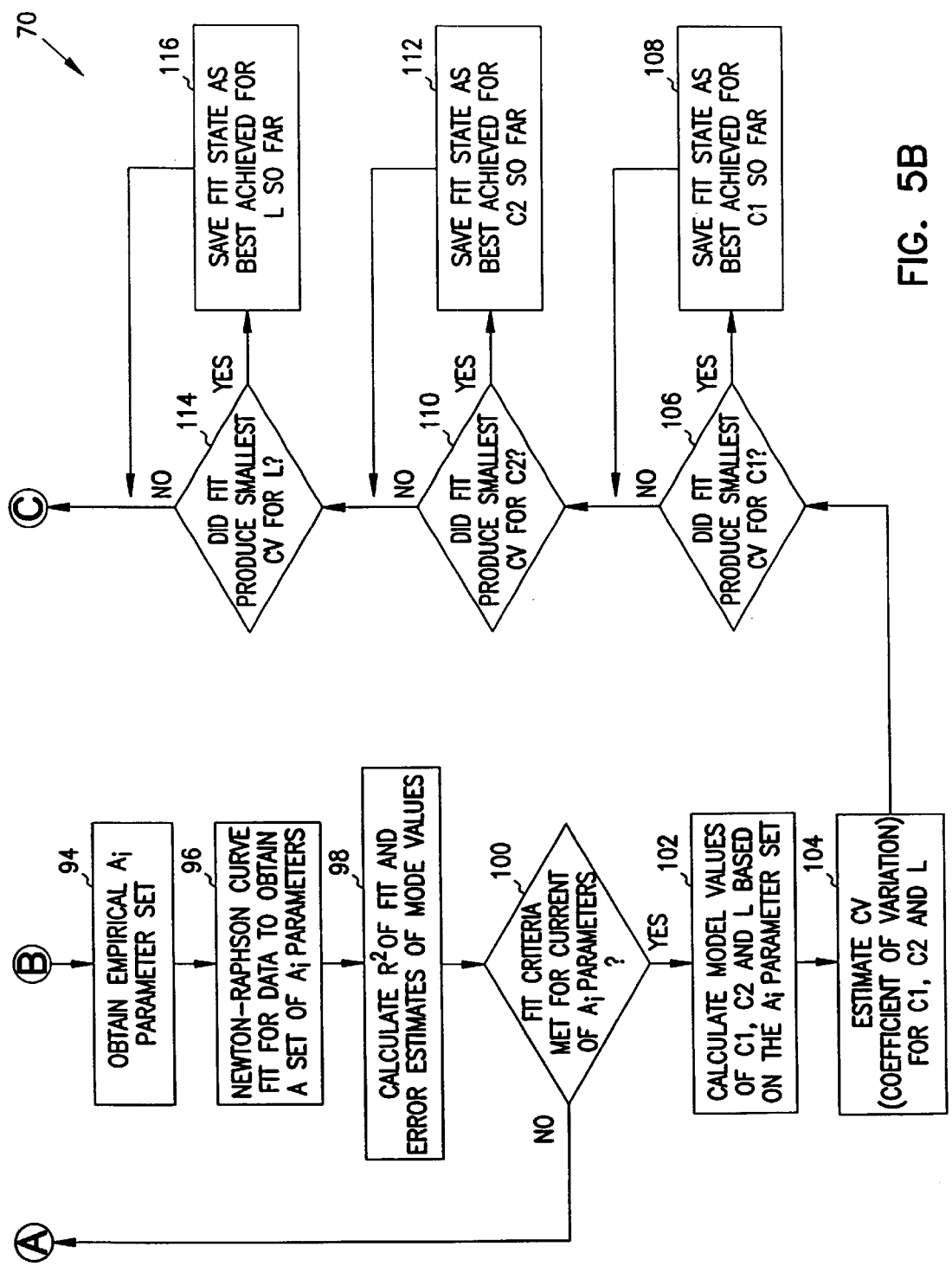

Referring to FIG. 5, there is illustrated an overview of the step 60 for analyzing selected beats. The process 70 of step 60 begins with a check to determine if a predetermined number of beats has been analyzed successfully (72–74), and, if so, proceeds to calculate the weighted averages of variables (76), the generation of a representative ensemble beat for display (78), and output of the results from the analysis (80). The beat length of the ensemble beat is assigned to the median beat length of all of the beats included. The ensemble beat is generated by averaging the data values across beats point by point using the upstroke point of each beat as the fiduciary point. The reported $C_1$ and $C_2$ parameters are taken as the weighted average of measures across at least five (5) and at most ten (10) beats, according to one example embodiment. The values are weighted by the ratio of the $R^2$ of the fit to the propagated error variance of the fit (model), as described more fully below.

If beat analysis is not complete, the process 70 obtains a beat for analysis (82). If there are no more diastolic data sets for the current beat, and the fit criteria are met for $C_1$, $C_2$ and L (84–86), the running sums for all variables are calculated (88). If the fit criteria are not met, the process returns to step 72.

If there are more data sets for a current beat, a diastolic data set for the current beat is obtained by scanning left to right across the near-notch region (NNR) of the digitized beat (90). Step 90 includes determining the near-notch region to be scanned for a beat and selecting the diastolic portion of a beat to analyze based on the current scan location and end diastolic mark.

If not all empirical $A_i$ parameter sets have been applied (92), a parameter set is obtained (94). A Newton-Raphson curve fit of data is performed to obtain a final set of $A_i$ parameters from the empirical starting point (96), and a calculation of $R^2$ of fit and error estimates of model data is performed (98). Curve fitting for a given diastolic data set and model parameters are driven by minimization of the mean square error agreement between the modeled arterial waveform and the actual data. For a given fit, the coefficient of determination ($R^2$ value) is used to determine whether a particular fit meets a goodness of fit standard, taken in this example embodiment as an $R^2$ greater than or equal to 0.975, as more fully described below.

If the fit criteria are not met (100), the process returns to step 92 and a different set of starting empirical $A_i$ parameters are obtained and the waveform re-fitted; if the criteria are met, the process proceeds to calculation of model values $C_1$, $C_2$ and L based on the this $A_i$ parameter set (102). An estimate of the coefficient of variation ($CV_e$=propogated error of value unadjusted for SVR or pressure error, divided by the value) is then calculated (104) for $C_1$, $C_2$ and L. If the fit produced the smallest $CV_e$ for $C_1$ (108), it is saved (108), for example in RAM 22 or in the storage device 24. Similar checks and saves are done for $C_2$ and L (110–116), and the process returns to step 84. If more data sets are obtainable for the beat by scanning the near-notch region, steps 90–116 are repeated. Thus, the particular fit (model) on a beat will be accepted to later contribute to the $C_1$ or $C_2$ value reported if it produces a minimization of the $CV_e$. for that measure as the dicrotic start region is scanned. The near notch region is a region of the arterial waveform just surrounding the notch. In the above-noted process, the starting point for the diastolic data set is taken from an initial point in that region, and then moved forward until all sets have been considered.

Thus, by this process, each near-notch region, identified by the scanning over a range of diastolic starting locations, produces independent values of $C_1$, $C_2$ and L. The limits of the scan range or window are taken as the location of the first positive going zero crossing of the second derivative to the subsequent negative going zero crossing of the second derivative, surrounding the notch point. A maximum scan window is defined to handle the case where the second zero crossing does not occur, as described more fully below.

Thus, as described above, process 70 applies a set of initial empirical model parameter values and a curve fitting algorithm such as the Newton-Raphson technique to the diastolic portion of the beat to obtain resulting curve fitting parameter values. If these parameter values meet the selection criteria for the regression between the model and data, the values are saved. If not, the next set of empirical model parameters are applied and the process repeated. This process is repeated for each scan location in a given beat so that at the end of beat analysis there is saved the fit state that results in the smallest estimated coefficient of variation, $CV_e$, value for each of $C_1$, $C_2$ and L independently.

Finally, the process determines whether the best saved fits for $C_1$ and $C_2$ both meet the criteria for the regression between model and data ($R^2$>=0.975). If so these fit states are saved as representative fits for the given beat and the next beat processed. If both $C_1$ and $C_2$ do not meet the criteria, then the results for the beat are not included and the process proceeds to analyze the next beat. This procedure is then repeated until a minimum acceptable number of beats (e.g., 5 to 10 beats) have been analyzed and accepted. The hemodynamic values are then calculated as the average values for these beats. The model values of $C_1$, $C_2$ and L are taken as the weighted average of the respective values from these beats. The weighting factor is the $R^2$ coefficient of determination regression value divided by the propagated error variance value for the particular measure. In addition, a representative arterial blood pressure waveform for visual display is generated as the average or ensemble of all the beats cross correlating at, or above,0.95.

Beat Marking Routines

The purpose of beat marking is to demarcate the individual beats contained in a collection of blood pressure waveform data. Marking the beats allows the individual beats to be examined separately and allows operations between beats like averaging all beats together or cross correlating individual beats together. As illustrated in FIG. 4, the following locations are marked for each beat: the upstroke point (onset of systole) A, peak systole B, dicrotic notch region C, end diastole D and the marks bracketing the near-notch scan region L-R, as determined as set forth above and in more detail below.

The upstroke mark (onset of systole) is taken as the prior minimum to the point at which the pressure change between data points five samples apart exceeds 10 mmHg. The peak systole mark B is taken as the peak or highest value for the beat. The dicrotic notch mark C is determined as outlined below. The diastolic mark D for the ith beat is initially taken as the upstroke mark of the ith+1 beat. Subsequently, the distal portion of the diastolic range is scanned to identify the point at which the decay ceases to be monotonically decreasing by less than about 0.1%. This point is marked as the end of diastole, or mark D. The value 0.1% is not strictly critical, but is a good estimate of where to spot the end of the monotonic decrease. Other values around 0.1 % are also acceptable to some degree.

Figure 6:
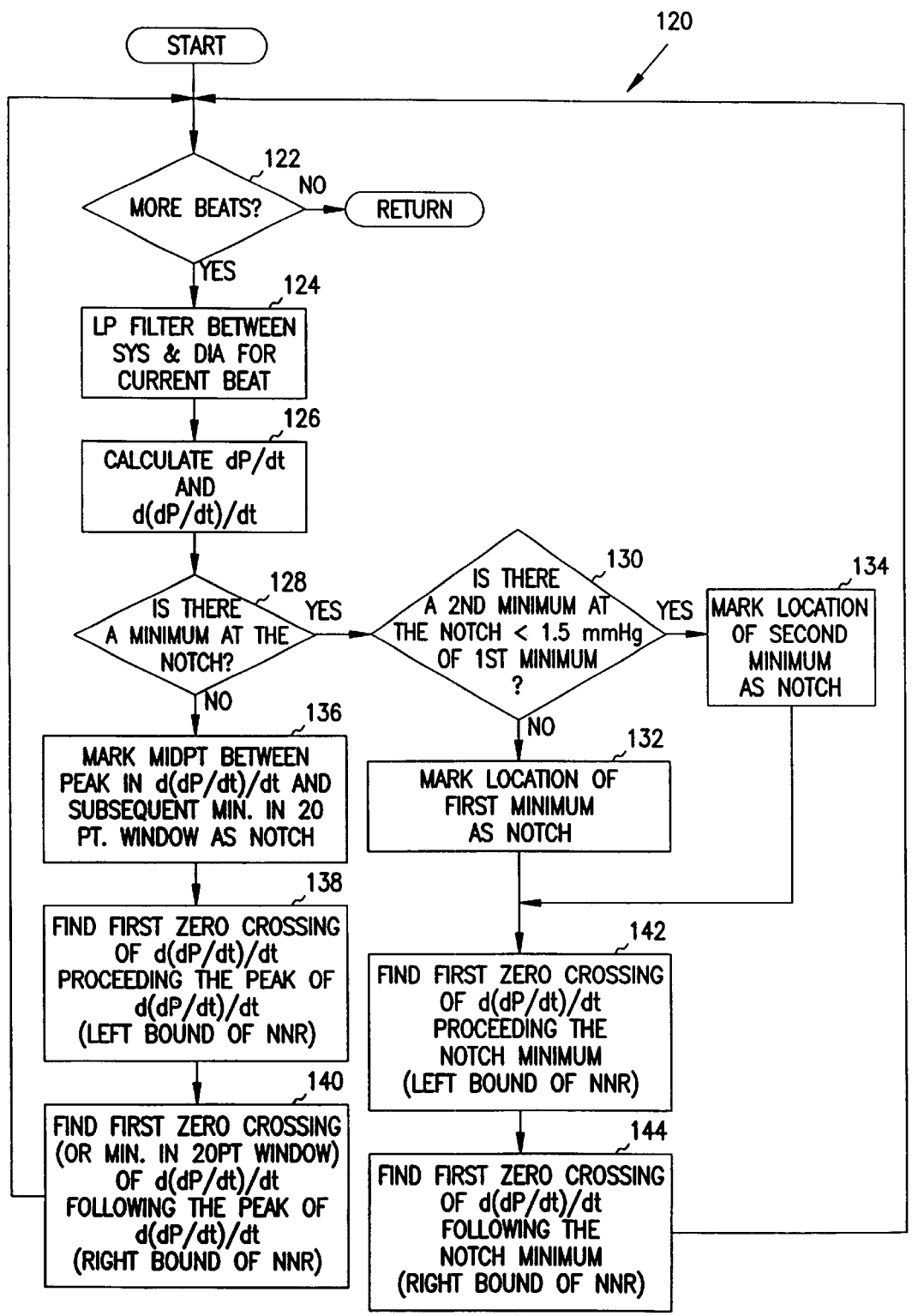
FIG. 6 illustrates the dicrotic notch marking process according to one example embodiment of the present invention.

Referring to FIG. 6 there is shown a simplified flow chart of the process 120 for locating the dicrotic notch features. Process 120 processes beats in steps 122–144. The first step (124) for each beat is to apply a low pass filter to the waveform data between the mark of systole and diastole for the current beat. Because the derivative process amplifies noise, filtering is used to minimize this undesired effect. An eight (8) pole, 15 Hz lowpass Butterworth filter with 6.026 db attenuation at the corner frequency is utilized to filter the region where derivatives are applied. The first derivative and second derivative of this waveform diastolic data set is calculated (126). The first derivative is used to determine if a notch minimum exists (128). If a single minimum exists it is taken as the notch location (132). If a second minimum exists in this range whose minimum value is less than 1.5 mmHg of the first minimum then it is taken as the minimum location (134). If no notch minimum is found, the second derivative is utilized to identify the notch location. The mid point between the peak of the second derivative and the subsequent minimum in a 20 point window from the peak is taken as the notch location (136). Finally the near notch region is identified as in (138–140) if no minimum existed or as in (142–144) if a minimum was identified. The only difference between the two is the point around which the zero crossings of the second derivatives are identified. In the first case if there is no second derivative zero crossing (140), the first local minimum in a twenty (20) window from the peak of the second derivative is found.

Selecting Beats for Further Analysis

Step 58 performs a beat to beat cross correlation using Pearson's cross-correlation to determine a dominant family of beats, and a heart rate variability restriction is applied in order to select a group of heart beats for further analysis. Beats are accepted that are within ±5% of the median beat length. The group with the greatest cross correlation coefficients with other beats meeting the criteria is taken as the dominant family of beats. The heart rate variability restriction limits the number of beats in the dominant family. Preferably, three groupings are made based on the median beat length (MBL) of all the beats. Group 1 contains beats of length between 0.85*MBL and 0.95*MBL. Group 2 contains beats of length between 0.95*MBL and 1.05*MBL. Group 3 contains beats of length between 1.05*MBL and 1.15*MBL. The grouping with the most number of beats, most often the middle group, is used for subsequent ensembling and analysis.

Curve Fitting to Diastolic Decay of a Beat

As noted above, the example process of the invention utilizes a modified Newton-Raphson or equivalent curve fitting technique for determination of the model parameters for the above noted third-order equation. The process involves an iterative process to minimize the difference between the actual data and the model. The routine of the example embodiment utilizes a minimum of five initial empirical parameter sets as a starting point in the iterative solution for the curve fitting process, but an alternate embodiment may add additional sets generated in a pseudo-random fashion or in such a way as to span parameter space in an efficient manner. For instance, one might search the corners of the parameter space ($2^5=32$ corners).

The process utilizes at least one and at most five (5) sets of empirical 'A' parameters for each diastolic waveform data set analyzed within a beat. Multiple waveform data sets are generated by the process because a range of starting locations are used that cover the transition from the systolic phase of the pressure wave to the diastolic phase of the pressure wave, as noted above. For a given set of initial 'A' parameters and start location for the diastolic curve, the process (96) utilizes an iterative curve fitting routine in order to minimize the difference between the model and the actual acquired diastolic pressure data. The initial empirical 'A' parameters are copied at the beginning of the process, are modified in the curve fitting process, and result in a final set of 'A' parameter vaules.

The currently preferred empirical 'A' parameter values are represented below. The groups are tried in the order they appear.

|  | $A_1$ | $A_2$ | $A_3$ | $A_4$ | $A_5$ | $A_6$ |
|---|---|---|---|---|---|---|
| Group 1 | * | 0.8 | 5.0 | 2.0 | 10.0 | 6.0 |
| Group 2 | * | 0.75 | 30.0 | 20.0 | 40.0 | 1.75 |
| Group 3 | * | 0.8 | 40.0 | 8.0 | 8.0 | 6.0 |
| Group 4 | * | 0.5 | 20.0 | 10.0 | 20.0 | 1.0 |
| Group 5 | * | 0.479 | 28.064 | 8.352 | 13.482 | 2.125 |

"*" parameters are computed as $A^1 = P_0 - A_3 \cos A_6$. Other sets of initial empirical A parameters could be generated in a pseudo-random fashion, to extend this set of empirical 'A' parameters.

Preferably, the following transformations govern the generation of 'A' parameters for each iteration in the curve fitting process:

$$\Delta A = (J^T J)^{-1} J^T D$$

$$A_{new} = A_{old} + w \Delta A$$

where $$A = (A_1, A_2, A_3, A_4, A_5, A_6)$$

$$J = \begin{pmatrix} \frac{\partial P_0}{\partial A_1} & \cdots & \frac{\partial P_0}{\partial A_6} \\ \vdots & \ddots & \vdots \\ \frac{\partial P_n}{\partial A_1} & \cdots & \frac{\partial P_n}{\partial A_6} \end{pmatrix}$$

Other embodiments might have w vary between $0.05 \leq w \leq 0.5$ but the example embodiment described here utilizes a value of 0.5. D is the difference vector between the actual data and the model fit for a given set of 'A' parameters.

Figure 7A:
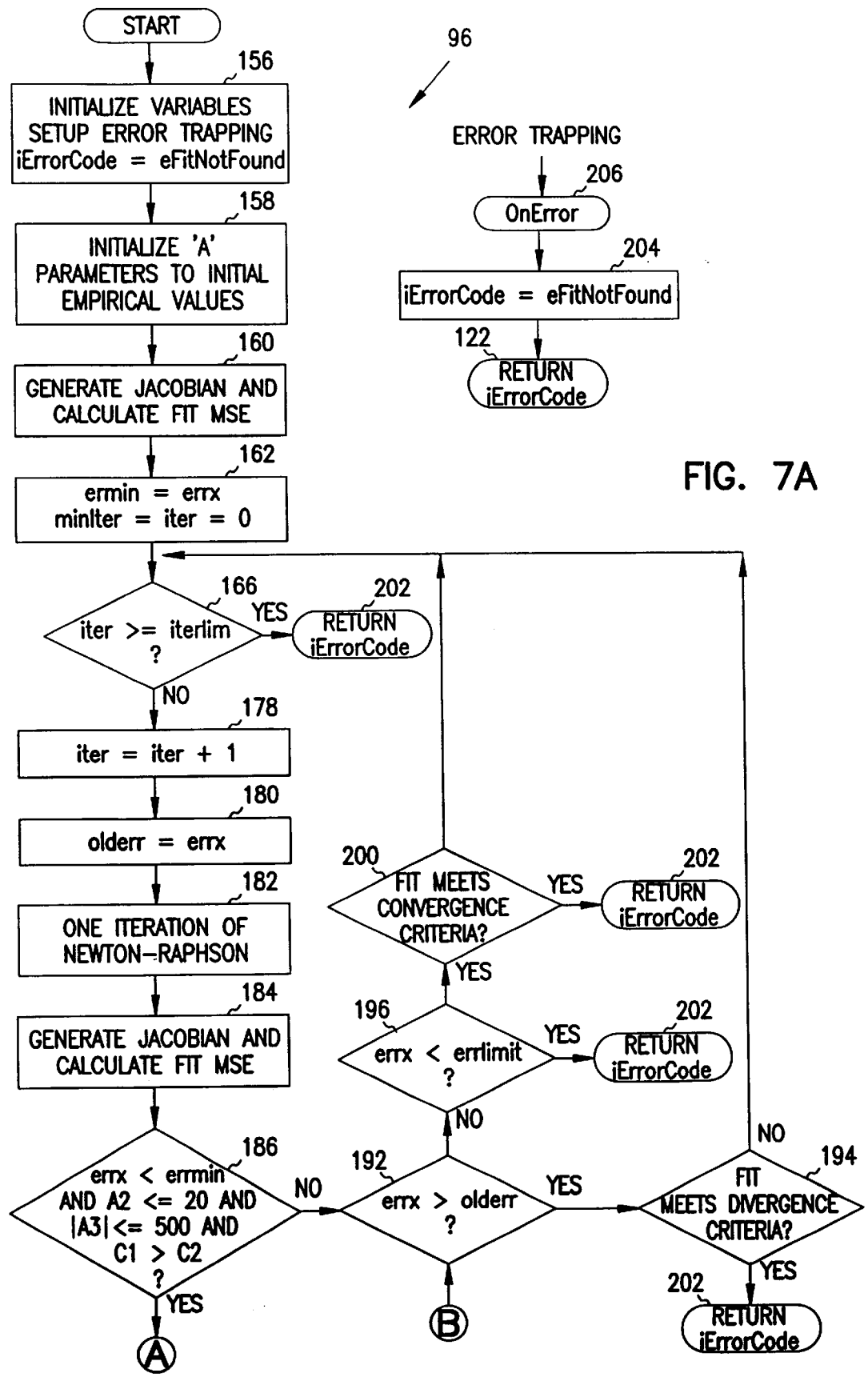
FIGS. 7A and 7B together form FIG. 7, which illustrates an example process for finding the best fit 'A' parameters for a diastolic waveform diastolic data set according to the present invention.
Figure 7B:
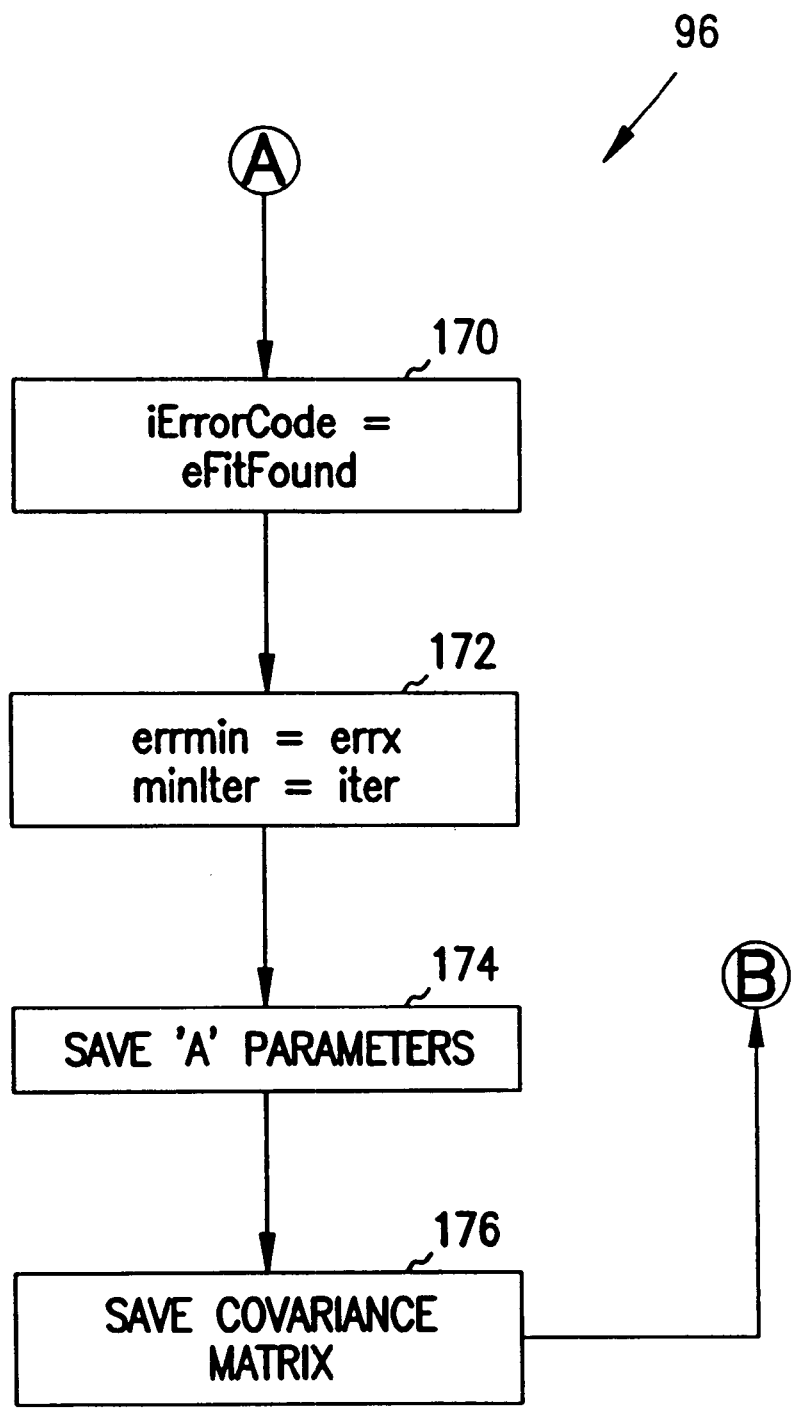

Referring to FIG. 7, there is illustrated a simplified flow chart for the process for curve fitting. This is an expansion of process 96 illustrated in FIG. 5. Process 156 initializes variables, sets up error trapping and sets iErrorCode to efitNotFound. Process 158 copies initial 'A' parameter values from the current empirical values. Process 160 begins with the generation of the Jacobian matrix and a calculation of the initial mean square error of fit (errx) of the starting curve fit, and this value is then set equal to the current minimum (errmin) (162). A check is made to see if the current iteration (iter) is less than the iteration limit (iterlim) (166). If not less, the iteration limit (50) is reached and the process returns (202).

If the iteration maximum has not been reached, the iter counter is incremented (178) and the variable olderr (old error) is set to errx (180). One curve fit iteration is performed to generate a new set of A parameters (182). The Jacobian matrix is generated and the errx for this fit is calculated (184). If errx is less than errmin and $A_2<=20$ and $|A_3|<=500$ and $C_1>C_2$ (186), the process proceeds to step (170). Otherwise, it proceeds to step 192. At step 170, iErrorCode is set to eFitFound to indicate that an acceptable fit was found. Errmin is set to errx and miniter is set to iter (172). The current 'A' parameter values are saved (174) and the covariance matrix is saved (176). The process continues at 192.

At step 192, errx is checked to see if it is greater than olderr and if yes the rate of error increase is checked (194). If the rate of increase exceeds a desired threshold, the process is taken to be diverging and returns (202), otherwise the process continues with the next iteration (166).

If errx is not greater than olderr, the process proceeds to check if errx is less than a desired error limit (196). If so the process returns (202), otherwise errx is checked to see if it is less than or equal to a desired percentage or ratio of olderr and thus has met a convergence criteria (200). If the fit is not improving (200), the process returns (202). If the process does not currently meet the convergence criteria the process continues (166). Error trapping is handled by (206). If a numerical error occurs, iErrorCode is set to eFitNotFound (204) and the process returns (202).

The above process identifies the best fitting set of 'A' parameters for a given diastolic data set and initial empirical 'A' parameter set.

Curve Fitting Standards

As noted, the curve fitting routine receives the data to be fit and an initial set of empirical values for the model parameters. The routine modifies the set of parameters by minimizing the mean square error between the actual data and the model fit, and produces an actual mean square error value that results from the fit. In the process, the objective is to achieve the best estimates for compliance by performing multiple analyses aimed at finding the best set of 'A' parameters to fit the waveform data.

The goodness of a curve fit is assessed by the coefficient of determination and is calculated as follows:

$$R^2 \cong 1 - MSE/\text{DiaVar}$$

$$\text{DiaVar} = \frac{1}{n_{initial}}\left(\sum (y - \bar{y})^2\right)$$

$$MSE = \frac{1}{n}\left(\sum (y - \hat{y})^2\right)$$

where $n_{initial}$ is taken as the length of diastole from the left most scan point to the end of diastole.

n is taken as the length of the current diastolic data set being fit.

y is the actual data $\bar{y}$ is the mean of the data $\hat{y}$ is the model fit to the data It is preferred in the example embodiment herein disclosed that criteria for an acceptable curve fit is a coefficient of determination value, $R^2$, equal or greater than 0.975.

The curve fitting is performed by a standard Newton-Raphson routine, which receives the data to be fit, and an initial 'A' parameter set, and returns either a set of final 'A' parameters and their estimated errors, or a return value indicating that a fit could not be found. If a fit is not found, or if the resulting parameters do not meet the standards for an acceptable fit, then the curve fitting is repeated using a different set of initial empirical parameters. It is assumed that the parameter set that failed may have fallen into a chi-squared local minimum, and that by starting the parameter search in a different area of parameter space, a lower minimum will be found that satisfies the curve fitting standards. The list of initial empirical parameters that is used begins with five sets as set forth above that have been found empirically to provide success in almost all cases. One embodiment could add additional sets to be utilized to attempt to cover unique regions of parameter space and/or to add some randomly generated sets. If none of these starting sets find an accepted fit meeting all of the criteria, then the curve fitting is said to have failed, and the model cannot be applied to such a set of diastolic data.

Selecting the Appropriate Data Set for a Beat

A successful curve fit to a diastolic data set establishes a set of model parameters which determines a $C_1$ and $C_2$ value for the beat. It has already been described how data set boundaries are determined by waveform marking and how a single curve fit is obtained. Described below is how a subset of diastolic data within the data boundaries is chosen for the curve fitting and how compliance values are subsequently calculated.

The modified Windkessel is designed to model diastole from beginning to end. Traditionally this means the start of the data set is the dicrotic notch point, and the end of the data set is the upstroke of the next beat. Deviation from tradition for the end of the data set is described above. Described below is how selection of the starting point deviates from tradition. The impetus for finding a new way of selecting the starting point for curve fitting results from three observations when using the traditional method: first, many arterial waveforms simply lack a dicrotic notch, second, the timing of a notch minimum in the proximal aorta is not necessarily the same as the peripheral arteries, and third, a number of human subjects show excessive variation in repeated compliance measurements. In notchless arterial waveforms, any particular point is difficult to justify. If a point is chosen too early, then part of systole is included. If a point is chosen too late, then a crucial part of early diastole may be left out. In persons who show excessive variability on repeated measures, it is often the case that two measurements are very close to one another, while only a third is vastly different. This suggests that a consistent compliance value is being clouded by an occasional outlier.

In an effort to find a suitable starting point for notchless arterial waveforms, the starting point for the diastolic data set is allowed to vary over a range around which a notch would normally appear, termed the "near notch region." A curve fit is performed and a compliance is obtained once for each starting point. By doing this it is found that many starting points produce roughly the same compliance value, while other starting points produce wildly different values. Again, although it seems as though a characteristic compliance value exists, it is difficult a priori to know which starting points will produce the best estimate of that value.

The example embodiment of the present invention utilizes the theory that all the starting points are producing estimates for the same value, only with different levels of confidence. Every measurement has associated with it a level of confidence. To test the theory, an estimation of the precision for each compliance value is needed.

The estimate used is based on the notion of "propagation of errors" and is given by:

$$\text{Var}(f) \approx g(A) \cdot C \cdot g(A)$$

where

Var(f) is the variance of f;
f=f(A) is the formula for $RC_1$, $RC_2$, or L/R evaluated at A;
$A=(A_1, A_2, A_3, A_4, A_5, A_6)$;
$g(A) = \vec{\nabla} f$ is the gradient of f w.r.t. A, evaluated at A;
$C=[J^T J]^{-1}$ is the covariance matrix at A that is returned from curve fitting, and where the pressure error is assumed to be 1 mm Hg; and
J is the Jacobian matrix for P(t, A) w.r.t. A where P (t, A) is the present model for diastolic pressure.

This expression gives a measure of the expected error in, e.g., $RC_1$. For this implementation, the error in R (systemic vascular resistance) is assumed to be equal to 0, but there are numerous ways of estimating an error for R as well, and thus modifying the total error estimate. The assumption that the pressure error be 1 mm Hg is inconsequential if it is assumed that this error is constant over the entire data acquisition, since it cancels out of the equation for the weighted average values. R does not exactly cancel out, since it varies beat by beat, but no increased performance has been seen in our experiments by accounting for this effect.

So, the final weighted average is given by:

$$\hat{f}_{final} = \frac{\sum_i \frac{r_i^2}{\text{Var}(f_i)} \hat{f}_i}{\sum_i \frac{r_i^2}{\text{Var}(f_i)}}$$

where the summation is taken over all of the analyzed beats;
$\hat{f}_{final}$ is the final value of the model parameter;
$r_i^2$ is the coefficient of determination from the curve fitting process;
each $f_i$ is chosen at the near notch range value which resulted in the smallest Var($f_i$); and
the hat symbol (^) indicates the value is adjusted appropriately for R (e.g., $RC_1$ is divided by R).

Precision

Precision was determined by taking the population average of the coefficient of variations in human research subjects who had triplicate measurements. When the above techniques of noise reduction through multiple samplings and a priori elimination of expected outliers were applied and compared with analysis of a single averaged beat at a single start point, the average $CV_e$ dropped from 14.5% to 9.5% ($C_1$) and from 24.9% to 13.8% ($C_2$) for control or normal subjects, that is persons without obvious cardiovascular disease. For subjects exhibiting cardiovascular disease, that is, non-normals, the improvements were 14.5% to 11.0% ($C_1$) and 30.2% to 19.9% ($C_2$). By repeating measurements on an individual, it is easy to obtain precision values for arterial compliance. For precision, one needs only compare measurements to each other. While the foregoing improvements are believed to be true, they are not presented herein as proof of the efficacy of the embodiments of the present invention, and should not be relied upon for any such purpose.

Accuracy

An important quality of a measure is how well it estimates the true value of what it purports to estimate. It is fairly well established in the worldwide medical literature that arteries stiffen as one gets older. Therefore, databases of blood pressure waveforms obtained invasively and non-invasively from men and women across a wide age range were used to examine this relation. This aging data supplies an acceptable qualitative measure of accuracy.

To test the expected decrease in arterial compliance with age, a database of 115 healthy male and female subjects between the ages of 19 and 75 was analyzed and compliance plotted versus age. When the analyses with and without noise reduction were compared, the $R^2$ value of the correlation of $C_1$ and $C_2$ with age improved considerably. The $R^2$ values were 0.25 or better for the measures. Additional confidence in these measures was obtained by examining the compliance values from several groups and comparing them to what the expected result should be. Those expected to have reduced arterial compliance because of hypertension, smoking tobacco products, coronary artery disease, or post-menopausal status should have lower compliance when compared to controls. In each case, non-normals had compliance values between 10% and 35% lower than normals using the analysis approach of the example embodiment of the invention herein described. Again, while the foregoing analysis is believed to be true, it is not presented herein as proof of the efficacy of the embodiments of the invention set forth herein, and should not be relied upon for any such purpose.

Modified Windkessel Model

As noted above, the example embodiment of the present invention uses the modified Windkessel model of the vasculature, and produces as output, the values $C_1$, $C_2$ and L, with R being calculated from mean arterial pressure and cardiac output. How mean arterial pressure and cardiac output are determined is not essential to the inventions claimed herein and are therefore not discussed further. However, method and apparatus for obtaining these measurements are described in U.S. '177 and U.S. Pat. No. 5,241,966, issued Sep. 7, 1993, and entitled "Method and Apparatus for Measuring Cardiac Output," the entire disclosure of which is herein incorporated by reference.

In addition to the $C_1$, $C_2$ and L parameters, the Total Vascular Impedance (TVI) may also be calculated and output as data from device 10 as the impedance function evaluated at the frequency of the measured heart rate w. The calculation for TVI is as follows:

$$TVI = \frac{1333.33 \sqrt{\left(\frac{1}{LC_2} - w^2\right)^2 + \left(\frac{w * 1333.33}{R * C_2}\right)^2}}{C_1 * \sqrt{\left(\frac{1333.33}{LRC_1 C_2} - \frac{1333.33 w^2}{RC_2}\right)^2 + \left(w^2 \left(\frac{1}{LC_1} + \frac{1}{LC_2} - w^2\right)\right)^2}}$$

where $w=(2\pi/60)*HR$

CONCLUSION

Thus, there is described herein above a method and apparatus for blood pressure waveform analysis which improves the reliability of the measured $C_1$, $C_2$ and L parameters utilizing the modified Windkessel model.

It is understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled. In particular, the invention(s) is not limited to application to human patients and subjects, and may also be used for animals. As such, the invention is generally applicable for use on all mammals which exhibit blood pressure waveforms to which the present invention may be applied. Furthermore, the invention(s) is not restricted to any particular model of the human vasculature, but has applicability to any model, electrical, fluid, mechanical or otherwise, that involves analysis of the blood pressure waveform. Moreover, both empirically and non-empirically determined starting values for the 'A' parameters can be used in order to find a fit that results in the desired minimization of error(s).

What is claimed is:

1. Apparatus for analyzing a digitized arterial blood pressure waveform comprising a computer programmed to carry out the steps of:
   a) identifying a diastolic portion of the waveform starting at an initial point;
   b) fitting a mathematical model of a curve to the diastolic portion of the waveform to determine a first set of curve fitting parameters;
   c) fitting the mathematical model to the diastolic portion of the waveform to determine a second set of curve fitting parameters;
   d) determining a first model parameter of an electrical analog model of a vasculature for each of the first and second sets of curve fitting parameters;
   e) determining an estimate of the error associated with each of the first model parameters; and
   f) selecting as superior the first model parameter with the least error associated with it.

2. Apparatus for analyzing a digitized arterial blood pressure waveform comprising
   a computer programmed to carry out the steps of:
   a) identifying a diastolic portion of the waveform starting at an initial point;
   b) fitting a mathematical model of a curve to the identified diastolic portion of the waveform to determine a first set of curve fitting parameters using a first set of initial condition parameters as an initial condition;
   c) fitting the mathematical model to the diastolic portion of the waveform to determine one or more additional sets of curve fitting parameters using one or more additional sets of initial condition parameters as initial conditions wherein each set of initial conditions are different from one another;
   d) determining a measure of the quality of fit for each set of curve fitting parameters to identify sets of parameters that meet a minimum requirement;
   e) determining one or more model parameters of an electrical analog model of the vasculature using each of the sets of the curve fitting parameters that meet the minimum requirement; and
   f) changing the identified diastolic portion of the waveform and repeating steps b, c, d and e.

3. Apparatus for identifying a diastolic portion including an onset of diastole and an end of diastole of a digitized arterial blood pressure waveform, the waveform including a dicrotic notch, comprising a computer programmed to carry out the steps of:
   a) identifying a near-notch region of the waveform around the dicrotic notch;
   b) marking a point on the waveform within the near-notch region as the onset of diastole; and
   c) marking a point representative of the end of diastole.

4. A method for analyzing a digitized arterial blood pressure waveform using a computer comprising the steps of:
   a) identifying a diastolic portion of the waveform starting at an initial point;
   b) fitting a mathematical model of a curve to the diastolic portion of the waveform to determine a first set of curve fitting parameters;
   c) fitting the mathematical model to the diastolic portion of the waveform to determine a second set of curve fitting parameters;
   d) determining a first model parameter of an electrical analog model of a vasculature for each of the first and second sets of curve fitting parameters;
   e) determining an estimate of the error associated with each of the first model parameters; and
   f) selecting as superior the first model parameter with the least error associated with it.

5. A method for analyzing a digitized arterial blood pressure waveform using a computer comprising the steps of:
   a) identifying a diastolic portion of the waveform;
   b) fitting a mathematical model of a curve to the identified diastolic portion of the waveform to determine a first set of curve fitting parameters using a first set of initial condition parameters as an initial condition;
   c) fitting the mathematical model to the diastolic portion of the waveform to determine one or more additional sets of curve fitting parameters using one or more additional sets of initial condition parameters as initial conditions wherein each set of initial conditions are different from one another;
   d) determining a measure of the quality of fit for each set of curve fitting parameters to identify sets of parameters that meet a minimum requirement;
   e) determining one or more model parameters of an electrical analog model of the vasculature using each of the sets of the curve fitting parameters that meet the minimum requirement; and
   f) changing the identified diastolic portion of the waveform and repeating steps b, c, d and e.

6. A method for identifying a diastolic portion of a digitized arterial blood pressure waveform comprising:
   a) identifying a region of the waveform around the dicrotic notch;
   b) marking a point on the waveform within the region as the onset of diastole;
   c) marking a point representative of the end of diastole; and
   d) marking the point representative of the end of diastole based on the decay of the waveform being monotonic.

7. A method for computer analysis of a digitized blood pressure waveform using an electrical analog model of the vasculature comprising identifying a superior model parameter from more than one model parameter wherein each model parameter is fit to the model, wherein the superior model parameter is determined by reference to an estimate of the error associated with each parameter.

8. The apparatus of claim 1, wherein the first model parameter is selected from the group:
   $C_1$=proximal or capacitive compliance, $C_2$=distal or reflective or oscillatory compliance, and
L=inertance.

9. The apparatus of claim 1, wherein the computer is further programmed to perform the step:
   g) identifying a near-notch region of the waveform around a dicrotic notch of the waveform, wherein the first set of curve fitting parameters are determined by defining the diastolic portion of the waveform to begin at a first point within the near-notch region, and the second set of curve fitting parameters are determined by defining the diastolic portion of the waveform to begin at a second point within the near-notch region, where the first and second points are different.

10. The apparatus of claim 2, wherein the one or more model parameters are selected from the group:
    $C_1$=proximal or capacitive compliance,
    $C_2$=distal or reflective or oscillatory compliance, and
    L=inertance.

11. The apparatus of claim 2, wherein the step f) of changing the identified diastolic portion of the waveform comprises:
    f)(1) identifying a near-notch region of the waveform around a dicrotic notch of the waveform; and
    f)(2) marking a point on the waveform within the near-notch region as the onset of diastole, wherein the point is different than the initial point.

12. The apparatus of claim 3, wherein the step a) of identifying the near-notch region comprises bracketing the dicrotic notch based on derivatives of the waveform.

13. The apparatus of claim 3, wherein the step a) of identifying the near-notch region comprises:
    a)(1) low-pass filtering the waveform between systole and end diastole for each beat to obtain a filtered waveform; and
    a)(2) bracketing the dicrotic notch based on derivatives of the filtered waveform.

14. The apparatus of claim 3, wherein the step a) of identifying the near-notch region comprises:
    a)(1) low-pass filtering the waveform between systole and end diastole for each beat using an eight-pole low-pass Butterworth filter with an attenuation of about 6 dB at its corner frequency to obtain a filtered waveform; and
    a)(2) bracketing the dicrotic notch based on derivatives of the filtered waveform.

15. The apparatus of claim 3, wherein the computer is further programmed to perform the steps:
    d) fitting a mathematical model of a curve to a first diastolic portion of the waveform starting at a first point within the region to determine a first set of curve fitting parameters;
    e) fitting the mathematical model to a second diastolic portion of the waveform starting at a second point different than the first point within the region to determine a second set of curve fitting parameters;
    f) determining a first model parameter of an electrical analog model of a vasculature for each of the first and second sets of curve fitting parameters;
    g) determining an estimate of the error associated with each of the first model parameters; and
    h) selecting as superior the first model parameter with the least error associated with it.

16. The method of claim 4, wherein the first model parameter is selected from the group:
    $C_1$=proximal or capacitive compliance,
    $C_2$=distal or reflective or oscillatory compliance, and
    L=inertance.

17. The method of claim 12, further comprising the step:
    g) identifying a near-notch region of the waveform around a dicrotic notch of the waveform, wherein the first set of curve fitting parameters are determined by defining the diastolic portion of the waveform to begin at a first point within the near-notch region, and the second set of curve fitting parameters are determined by defining the diastolic portion of the waveform to begin at a second point within the near-notch region, where the first and second points are different.

18. The method of claim 5, wherein the one or more model parameters are selected from the group:
    $C_1$=proximal or capacitive compliance,
    $C_2$=distal or reflective or oscillatory compliance, and
    L=inertance.

19. The method of claim 5, wherein the step f) of changing the identified diastolic portion of the waveform comprises:
    f)(1) identifying a near-notch region of the waveform around a dicrotic notch of the waveform; and
    f)(2) marking a point on the waveform within the near-notch region as the onset of diastole, wherein the point is different than the initial point.

20. A method for identifying a diastolic portion of a digitized arterial blood pressure waveform comprising the steps of:
    a) identifying a region of the waveform around the dicrotic notch;
    b) marking a point on the waveform within the region as the onset of diastole; and
    c) marking a point representative of the end of diastole, wherein the a) identifying the near-notch region comprises bracketing the dicrotic notch based on derivatives of the waveform.

21. A method for identifying a diastolic portion of a digitized arterial blood pressure waveform comprising:
    a) identifying a region of the waveform around the dicrotic notch;
    b) marking a point on the waveform within the region as the onset of diastole; and
    c) marking a point representative of the end of diastole, wherein the a) identifying the near-notch region comprises bracketing the dicrotic notch from a positive-going zero-crossing of a second derivative of the waveform to a following negative-going zero-crossing of the second derivative of the waveform.

22. A method for identifying a diastolic portion of a digitized arterial blood pressure waveform comprising:
    a) identifying a region of the waveform around the dicrotic notch;
    b) marking a point on the waveform within the region as the onset of diastole; and
    c) marking a point representative of the end of diastole, wherein the a) identifying the near-notch region comprises:
       a)(1) low-pass filtering the waveform between systole and end diastole for each beat to obtain a filtered waveform; and
       a)(2) bracketing the dicrotic notch based on derivatives of the filtered waveform.

23. A method for identifying a diastolic portion of a digitized arterial blood pressure waveform comprising:
    a) identifying a region of the waveform around the dicrotic notch;

b) marking a point on the waveform within the region as the onset of diastole; and c) marking a point representative of the end of diastole, wherein the a) identifying the near-notch region comprises:

a)(1) low-pass filtering the waveform between systole and end diastole for each beat using an eight-pole low-pass Butterworth filter with an attenuation of about 6 dB at its corner frequency to obtain a filtered waveform; and a)(2) bracketing the dicrotic notch from a positive-going zero-crossing of a second derivative of the waveform to a following negative-going zero-crossing of the second derivative of the filtered waveform.

24. The method of claim 7, wherein each one of the more than one model parameters are selected from the group:

$C_1$=proximal or capacitive compliance, $C_2$=distal or reflective or oscillatory compliance, and L=inertance.

25. A method for identifying a diastolic portion of a digitized arterial blood pressure waveform comprising the steps of:

a) identifying a region of the waveform around the dicrotic notch;

b) marking a point on the waveform within the region as the onset of diastole;

c) marking a point representative of the end of diastole;

d) fitting a mathematical model of a curve to a first diastolic portion of the waveform starting at a first point within the region to determine a first set of curve fitting parameters;

e) fitting the mathematical model to a second diastolic portion of the waveform starting at a second point different than the first point within the region to determine a second set of curve fitting parameters;

f) determining a first model parameter of an electrical analog model of a vasculature for each of the first and second sets of curve fitting parameters;

g) determining an estimate of the error associated with each of the first model parameters; and h) selecting as superior the first model parameter with the least error associated with it.

26. A method for computer analysis of a digitized blood pressure waveform using an electrical analog model of the vasculature comprising identifying a superior value of a first model parameter from more than one value of the first model parameter wherein each value of the first model parameter is determined from parameters fit to the model, wherein the superior value of the first model parameter is determined by reference to an estimate of the error associated with each value.

27. The method of claim 26, wherein each one of the more than one value for the first model parameter is based on a different starting point of a diastolic portion of the waveform.

28. The method of claim 26, wherein each one of the more than one value for the first model parameter is based on a different starting point of a diastolic portion of one beat of the form.

29. The method of claim 26, wherein the first model parameter is selected from the group:

$C_1$=proximal or capacitive compliance, $C_2$=distal or reflective or oscillatory compliance, and L=inertance.

30. The method of claim 20, further comprising:

d) fitting a mathematical model of a curve to the diastolic portion of the waveform to determine a first set of curve fitting parameters;

e) fitting the mathematical model to the diastolic portion of the waveform to determine a second set of curve fitting parameters;

f) determining a first model parameter of an electrical analog model of a vasculature for each of the first and second sets of curve fitting parameters;

g) determining an estimate of the error associated with each of the first model parameters; and h) selecting as superior the first model parameter with the least error associated with it.

* * * * *